United States Patent [19]
Wick

[11] 4,453,806
[45] Jun. 12, 1984

[54] EYE SAFE LASER TRANSMITTER

[75] Inventor: Raymond V. Wick, Albuquerque, N. Mex.

[73] Assignee: The United States of America as represented by the Secretary of the Air Force, Washington, D.C.

[21] Appl. No.: 339,261

[22] Filed: Jan. 13, 1982

[51] Int. Cl.³ .............................................. G02B 5/02
[52] U.S. Cl. ................................................ 350/431
[58] Field of Search ........................................ 350/431

[56] References Cited

U.S. PATENT DOCUMENTS

| | | | |
|---|---|---|---|
| 2,275,602 | 3/1942 | Beck et al. | 350/431 |
| 3,107,529 | 10/1963 | Johnston, Jr. | 73/339 |
| 3,343,449 | 9/1967 | Blackwell et al. | 88/23 |
| 3,561,842 | 2/1971 | Horton | 350/160 |
| 3,900,249 | 8/1975 | Tsunashima et al. | 350/431 |
| 4,111,561 | 9/1978 | Plummer | 356/225 |
| 4,155,630 | 5/1979 | Ih | 350/431 |

*Primary Examiner*—John K. Corbin
*Assistant Examiner*—Rebecca D. Gass
*Attorney, Agent, or Firm*—Donald J. Singer; Thomas L. Kundert

[57] ABSTRACT

An apparatus for converting a high intensity spatially coherent laser beam into a source of spatially incoherent radiation that retains the temporal, amplitude and frequency characteristics, and also the polarization, of the spatially coherent laser beam. A laser is oriented so that its coherent output beam falls on a transmissive optical lens which images the coherent beam onto the surface of a ground glass plate that has been etched with hydrofluoric acid to form a spatial diffuser. The radiation that emerges from the diffuser has been converted into spatially incoherent radiation that retains some important characteristics of the coherent beam, namely polarization and temporal coherence. The diffuser outputs a diverging beam of substantially incoherent radiation to a collimator that provides a collimated output beam that can be used in laser communicators, laser rangefinders and other laser field devices in an "eyesafe" mode.

4 Claims, 5 Drawing Figures

IMPROVEMENTS

EYE SAFE LASER TRANSMITTER

STATEMENT OF GOVERNMENT INTEREST

The invention disclosed herein has been assigned to the government and may be used by or for the government for governmental purposes without the payment of any royalty therefore.

BACKGROUND OF THE INVENTION

1. Field of the Invention

The invention relates to transmitters of laser radiation and, more particularly, the invention is concerned with making transmitters of laser radiation eyesafe.

2. Description of the Prior Art

It is a recognized problem that laser beams can damage the eyes and the damage can be caused in a small fraction of a second by a high energy laser beam. Tests on rabbits to determine the harmful effect of lasers have produced severe thermal lesions in the rabbits' eyes. One reason for this, aside from the transmitted intensity of the laser beam, is that pigmented tissue in the eye's retina absorbs more energy from laser beams than does ordinary tissue. A second reason is that spatially coherent radiation focuses to a diffraction limited spot which is very small. This in turn means a very high power density. Thus, the choroid membrane of the eyeball, which contains pigment cells, is very susceptible to laser damage. One suggested means for protecting the eye against laser radiation is goggles having thick opaque lens with a tiny hole in the center of the lens. The laser beam has to go through the center hole to reach the eye. This is unlikely and a cap shield around the center hole lends even more protection. However, it is still possible for a laser beam to enter the small hole and should this happen, the macula, or point of sharp focus on the retina of the eye, would be damaged. The victim would thereafter be able to see light and dark and gross objects, but the ability to focus sharply would be destroyed. It has also been suggested that narrowband optical fibers could be designed to attentuate the laser beam to safe levels while still passing sufficient other radiation to allow the person looking through the filters to see.

An attempt was made to convert a coherent beam of laser radiation into spatially incoherent radiation by reflecting the beam off a gold surface which had been dimpled by dropping 15 micron diameter steel balls on the surface. The dimpled gold diffusing surface area was tested by imaging a YAG laser on it, at a power density in excess of 100 megawatts per square centimeter (100 MW/CM$^2$). The surface structure was destroyed by evaporation of the gold.

There have also been protective devices disclosed in the art which function like a shutter. The shutter will supposedly permit full use of an optical system until needed and then the shutter will be capable of closing rapidly in response to harmful radiation. Hopefully, the shutterlike device will operate quickly enough to prevent eye damage. A number of such devices are disclosed in U.S. Pat. No. 3,561,842 issued to Billy M. Horton wherein the optical quality of both reflective and transmissive optical elements are destroyed by high intensity radiation. In the Horton devices, a polished surface material such as silicon monoxide is evaporated from a quartz lens by the radiation, leaving a roughened surface exposed that provides an optically diffusing surface that disrupts the beam from which protection is needed. This approach has the disadvantage, among others, of rendering the optical device using it inoperative. Also, this approach would alter the amplitude, frequency and polarization of the radiation so it would not be employed in a communications or rangefinder system.

Diffuser lens elements are also known in the camera art. These lens, as disclosed in U.S. Pat. No. 4,111,561 issued to William T. Plummer, have a roughened diffuser area that reduces the intensity of the light coming in on the optical axis of the camera. Such inventions are for use in cameras that utilize incoherent radiation and they would have no application in the protection of eyes from laser devices.

There is to date no satisfactory laser apparatus available for eliminating the high power, or energy density, on the retina of the eye. Neither is there a laser transmitter available for providing, at close ranges, a constant power, or energy density, on the retina due to the radiation source being focused to a finite image rather than a diffraction limited spot on the retina of the eye.

SUMMARY OF THE INVENTION

A primary object of this invention is converting high energy spatially coherent radiation into eyesafe spatially incoherent radiation without destroying properties of the coherent radiation such as temporal coherence, polarization, and monochromaticity, that makes the radiation useful in various optical devices.

A more specifically stated object of the invention is converting a beam of high energy, spatially coherent radiation into a beam of spatially incoherent radiation that retains the amplitude, frequency, wavelength, and polarization properties of the coherent beam.

These objectives are accomplished by inserting a diffuser into a laser device along the optical axis thereof. The laser device would include a high energy laser, a focusing or imaging lens for imaging the laser beam on the diffuser and a collimator for producing a nearly parallel beam from the diverging beam of incoherent radiation emanating from the diffuser. The laser beam must pass through the diffuser before exiting from the device to the surroundings in order to prevent the laser from causing eye damage. The diffuser is a ground glass plate that has been etched on one side, or both sides, with hydrofluoric acid to provide a high damage threshold light diffusing surface of a suitable finite area. Such etched ground glass plates are commercially available. Tests wherein such a diffuser has been irradiated at high power densities without any ill effects have proven that it is an excellent high damage threshold diffuser candidate. Experimental use of the invention confirmed that the device would produce polarized spatially incoherent radiation which is still frequency and amplitude stabilized.

DETAILED DESCRIPTION OF THE INVENTION

Figure 1A:
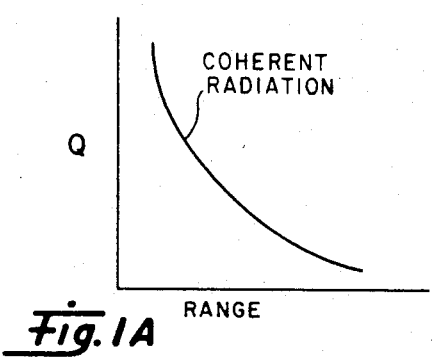
FIGS. 1a and 1b are graphs illustrating the relationships between the radiation power density, Q, in watts per square centimeter on the eye's retina and the range in meters.
Figure 1B:
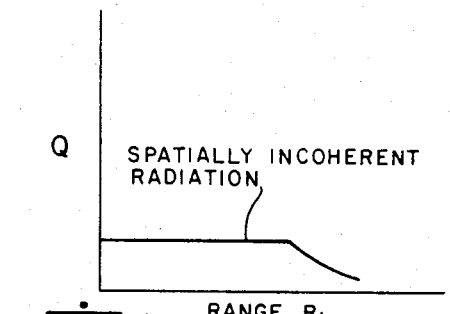

Spatially coherent radiation has the characteristic of always appearing as a point source (called-diffraction limited) to the retina of the eye, regardless of the range of the eye from the origin of the coherent radiation. Thus, all the energy in a coherent beam will be concentrated in a very small area. This image formed on the retina is nearly diffraction limited and varies in size only due to beam divergence of the laser. Beam divergence of any laser is very slight. At short ranges the power density on the retina, resulting from a diffraction limited image formed by spatially coherent radiation, will damage the retina. In FIG. 1a of the drawing is a graph showing how the power density Q of a diffraction limited spot, the image produced by spatially coherent radiation, varies with range. The curve appearing on the graph in FIG. 1b illustrates the power density Q on the retina of an eye for spatially incoherent radiation. Note that for spatially incoherent radiation the power density remains constant for all ranges up to range $R_L$ due to the fact that the incoherent source has a finite image. After range $R_L$ the source of incoherent radiation appears to the eye as a point source and the power density on the retina is a function of $1/R^2$, as is the power density for coherent radiation for all ranges. This means that for ranges less than $R_L$ the image size formed on the retina of the eye varies with the distance from the radiation source. Thus, when the eye is close to the source the image formed on the retina of the eye is large and the total energy in the beam of radiation forming the image is spread over a larger area. This keeps the power density Q down to a point where the eye is not damaged.

Figure 2:
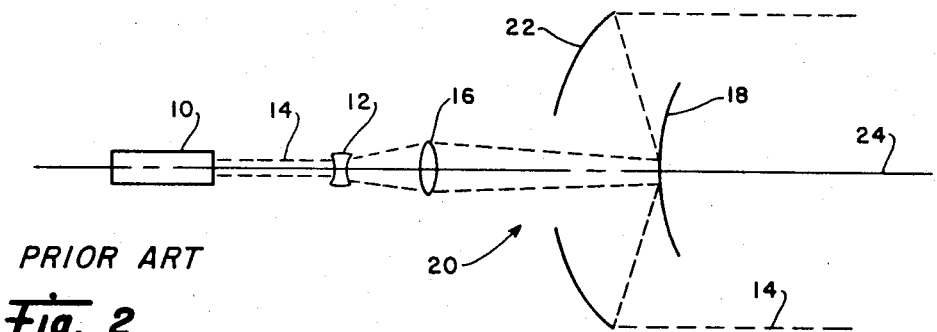
FIG. 2 is a schematic illustration of an exemplary prior art laser device that does not incorporate any eyesaving features.

Referring now to FIG. 2 of the drawing which illustrates a typical prior art laser beam transmitter. A laser 10 is directed at a diverging lens 12. Beam 14 from laser 10 is expanded by lens 12 before passing through converging lens 16 which focuses the beam on reflecting element 18 through a hole 20 in another reflecting element 22. The beam reflected from element 18 follows a path to reflecting element 22 which forms a collimated beam of coherent radiation having a desired cross-section and direction. All of the components of the transmitter shown in FIG. 1 are concentrically mounted about optical axis 24. The beam from this transmitter could be used in various applications mentioned previously.

Figure 3:
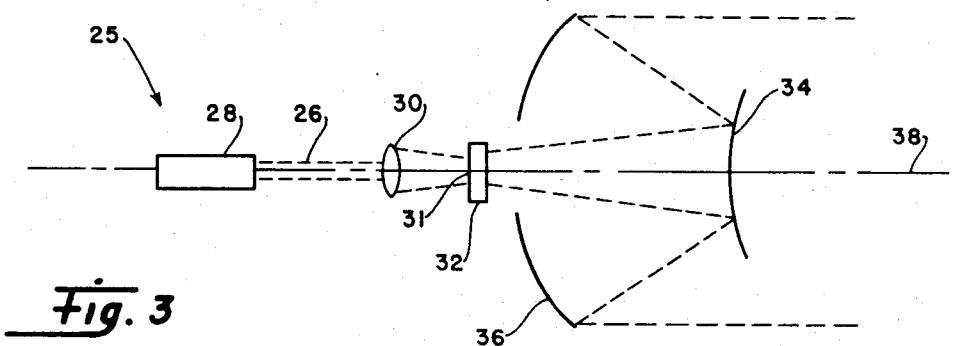
FIG. 3 is a schematic illustration of a laser device employing a diffuser to make the device eyesafe. In this embodiment reflective optical components are used to recollimate the beam of spatially incoherent radiation.

In FIG. 3 an eyesafe laser transmitter 25 is shown. A beam 26 of coherent radiation from laser 28 passes through lens 30 which images the beam on a microscopically etched dialectric window or diffusing area 31 on diffuser 32. Diffuser 32 is a ground glass plate that has one or both sides thereof etched with hydrofluoric acid. The laser radiation emerging from diffuser 32 has been converted to spatially incoherent radiation so that it focuses to a finite image on the retina of the eye. As mentioned above, image size on the retina becomes larger the closer the eye is to the source of radiation. The radiation from diffuser 32 is collimated by reflective elements 34 and 36 to provide a beam of spatially incoherent radiation that can be used in a number of applications where eye safe transmissions are needed. All the optical components of the FIG. 3 device are mounted concentrically on axis 38. Advantageous features of the beam produced by the FIG. 3 transmitter are numerous. Polarization of the original laser beam is maintained. Reflection and absorbance of the laser beam is minimized due to the fact diffuser 32 transmits 92% of the laser beam focused thereon. The scattering angle of diffuser 32 is well defined by the etching time of the diffusing surface. A 50-minute etching time for a spot 1 millimeter in diameter on ground glass produces nominally 750,000 scattering areas. The frequency and relative amplification of the laser beam is maintained. The beam of spatially incoherent radiation will spread more than a beam of spatially coherent radiation, but the spread need not be significant when the transmitter is used in relatively short range devices like that mentioned in this application.

Figure 4:
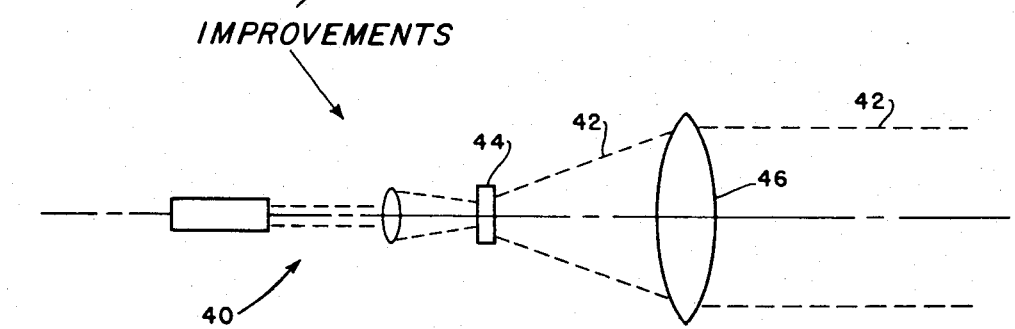
FIG. 4 is a schematic illustration of a configuration of the invention that could be used to illuminate a large number of optical components. In this embodiment the diverging beam of spatially incoherent radiation is collimated using transmissive optics.

The laser beam transmitter 40 shown in FIG. 4 is an alternate configuration of the invention that could be used to illuminate a more varied group of optical components. In this configuration radiation 42 from spatial diffuser 44 is collimated by lens element 46 to provide an output beam of spatially incoherent radiation.

In order for ground glass etched with hydrofluoric acid to be used as an incoherent spatial scatterer or diffuser for lasers, the ground glass must withstand very high power densities. For one particular project a 12-inch parabolic source reflector was required. In order to control the beam divergence from this 12-inch reflector it was necessary that the scatterer be illuminated in an area having a diameter between 1.2 mm. and 4 mm. Therefore, for the project the power density on the illuminated area of the diffuser would be from $5.8 = 10^9$ w/cm$^2$ to $5 = 10^8$ w/cm$^3$ for the respective spot areas. To test the etched ground glass diffuser it was radiated at several power densities with a YAG (Yttrium Aluminum Garnet-Crystal) laser system. The peak power density at the focused position was equal to 65 GW/cm$^2$ (GW = $10^9$ watts = gigawatts) This power density was irradiated on the surface for 2 minutes at 10 pulses per second. Therefore, 1200 pulses were impinged and there was no damage. Another irradiation was at a distance of 9.5 cm. from a 10.6 cm. focal length lens so the radiated spot on the diffuser had a diameter of 0.738 mm. and an average power density of $4.3 = 10^9$ w/cm$^2$. There was no sign of any damage to the diffuser after being irradiated for 2 minutes. Therefore, since the ground glass etched with hydrofluoric acid demonstrated an ability to withstand energy densities in excess of $4.0 = 10^9$ w/cm$^2$ (4.0 gigawatts/cm$^2$), and produce polarized spatially incoherent radiation that is frequency and amplitude stabilized, it is an excellent spatial diffuser for eyesafe laser transmitters. Tests of a laser transmitter incorporating the diffuser disclosed herein were very successful.

What is claimed is:

1. An eyesafe laser transmitter apparatus for converting a very high intensity spatially coherent laser beam into a high intensity beam of spatially incoherent radiation having a sufficient energy density to be useful while capable of being focused to a finite image on the retina of the eye rather than a diffraction limited spot, said apparatus comprising:

a laser that generates a beam of high energy spatially coherent laser radiation, transmissive optical lens means positioned adjacent said laser and in the path of said laser beam for imaging said laser beam, diffuser means for forming a high damage threshold diffuser surface to convert a beam of high energy spatially coherent radiation into a high intensity beam of spatially incoherent radiation while maintaining the polarization, amplitude and frequency characteristics of the laser beam, and controlling the angular divergence, said diffuser surface being positioned so as to have the laser beam imaged thereon by said optical lens, and collimating means positioned adjacent said diffuser means for receiving radiation from said diffuser means and providing a collimated output beam of spatially incoherent radiation, whereby an eyesafe laser transmitter satisfactory for use in laser rangefinders and communicators is provided.

2. The invention recited in claim 1, wherein said diffuser means comprises a fine ground glass plate having at least one surface thereof etched by hydrofluoric acid.

3. The invention recited in claim 2 wherein said collimating means is composed of transmissive components.

4. The invention recited in claim 2 wherein said collimating optical means is composed of reflective components.

* * * * *

UNITED STATES PATENT AND TRADEMARK OFFICE
CERTIFICATE OF CORRECTION

PATENT NO. : 4,453,806
DATED : June 12, 1984
INVENTOR(S) : Raymond V. Wick

It is certified that error appears in the above-identified patent and that said Letters Patent is hereby corrected as shown below:

```
Front page, in the title, change "Eye Safe" to --Eyesafe--.
Col 1, in the title, change "Eye Safe" to --Eyesafe--.
Col 2, line 4, delete "would" and insert --could--.

Col 4, lines 36, 37, 48 and 53, delete "=" and insert --x--.
```

Signed and Sealed this

Ninth Day of April 1985

[SEAL]

*Attest:*

DONALD J. QUIGG

*Attesting Officer*  *Acting Commissioner of Patents and Trademarks*